(12) United States Patent
Michel et al.

(10) Patent No.: US 9,272,054 B2
(45) Date of Patent: Mar. 1, 2016

(54) AGENTS FOR THE MOLECULAR IMAGING OF SERINE-PROTEASE IN HUMAN PATHOLOGIES

(75) Inventors: Jean-Baptiste Michel, Paris (FR); François Rouzet, Paris (FR); Dominique Leguludec, Paris (FR); Hervé Poras, Paris (FR); Marie-Claude Fournie-Zaluski, Paris (FR); Bernard Rogues, Paris (FR)

(73) Assignees: Institut National de la Sante et de la Recherche Medicale (INSERM), Paris (FR); Pharmaleads, Paris (FR); Assistance Publique Hopitaux de Paris, Paris (FR); Universite Paris Diderot-Paris 7, Paris (FR)

( * ) Notice: Subject to any disclaimer, the term of this patent is extended or adjusted under 35 U.S.C. 154(b) by 53 days.

(21) Appl. No.: 13/990,845

(22) PCT Filed: Dec. 5, 2011

(86) PCT No.: PCT/EP2011/071774
§ 371 (c)(1),
(2), (4) Date: May 31, 2013

(87) PCT Pub. No.: WO2012/072819
PCT Pub. Date: Jun. 7, 2012

(65) Prior Publication Data
US 2013/0243691 A1    Sep. 19, 2013

(30) Foreign Application Priority Data

Dec. 3, 2010    (EP) ...................................... 10306343
Apr. 7, 2011    (EP) ...................................... 11305405

(51) Int. Cl.
| A61K 51/00 | (2006.01) |
| A61M 36/14 | (2006.01) |
| A61K 49/00 | (2006.01) |
| A61K 49/14 | (2006.01) |
| A61K 51/08 | (2006.01) |

(52) U.S. Cl.
CPC ............. *A61K 49/0004* (2013.01); *A61K 49/14* (2013.01); *A61K 51/08* (2013.01); *A61K 51/088* (2013.01)

(58) Field of Classification Search
CPC ........... G01N 33/5008; G01N 33/5088; A61K 49/00; A61K 49/14; A61K 51/00; A61K 51/04; A61K 51/06; A61K 51/08; A61K 51/088; A61K 49/0004; A61K 2123/00; A61K 2121/00; A61K 38/00; A61K 49/0002; A61K 49/04; A61K 49/13; A61K 49/06
USPC ........... 424/1.11, 1.65, 1.69, 1.81, 1.85, 1.89, 424/9.1, 9.3, 9.4, 9.5, 9.6, 9.7, 9.8; 530/300, 330, 331; 534/7, 10–16; 514/1, 1.1, 21.8

See application file for complete search history.

(56) References Cited

U.S. PATENT DOCUMENTS

| 5,916,877 A | 6/1999 | Powers et al. |
| 2005/0136492 A1 | 6/2005 | Phelps et al. |

FOREIGN PATENT DOCUMENTS

| CA | 1335725 C | 5/1995 |
| EP | 0339684 A2 | 11/1989 |
| WO | 2004/064870 A2 | 8/2004 |
| WO | 2010/103475 A2 | 9/2010 |

OTHER PUBLICATIONS

Rasmus et al., "Fluorescently labeled inhibitors detect localized serine protease activities in *Drosophila melanogaster* pole cells, embryos, and ovarian egg chambers", Histochemistry and Cell Biology, Jan. 1, 2005, pp. 51-60, vol. 123, No. 1.
Abuelyaman et al., "Fluorescent Derivatives of Diphenyl [1-(N-Peptidylamino)Alkyl] Phosphonate Esters: Synthesis and Use in the Inhibition and Cellular Localization of Serine Proteases", Bioconjugate Chemistry, Sep. 1, 1994, pp. 400-405, vol. 5, No. 5.
Woessner et al., "Connective Tissue Breakdown in Ovulation", Steroids, Nov. 1, 1999, pp. 491-499, vol. 54, No. 5, Elsevier Science Publishers, New York, NY.
Jaffer et al., "In Vivo Imaging of Thrombin Activity in Experimental Thrombi With Thrombin-Sensitive Near-Infrared Molecular Proble", Arteriosclerosis, Thrombosis, and Vascular Biology, Aug. 8, 2002, pp. 1929-1935, vol. 22, No. 11, Lippincott Williams & Wilkins, US.

*Primary Examiner* — D L Jones
(74) *Attorney, Agent, or Firm* — Whitham Curtis Christofferson & Cook, PC (57) ABSTRACT

The present invention is directed to the use of an irreversible ligand of a serine protease selected from the group consisting of leukocyte elastase, thrombin, tissue plasminogen activator (t-PA) and plasmin for the molecular imaging of said serine protease and the diagnosis of pathophysiological conditions associated with said serine protease activity.

20 Claims, 7 Drawing Sheets

PL714: DOTA-Gly-DPhe-Pro-Arg-cmk
PL720: DTPA-BnNHCS-Gly-DPhe-Pro-Arg-cmk

| Compound | Thrombin (Ki) | uPA (Ki) | Plasmin (IC 50) | tPA (IC50) |
|---|---|---|---|---|
| PL 714 | 1.09 nM | 1.46 µM | > 10µM | 0.55 µM |
| PL 720 | 1.35 nM | 27.1 µM | 0.75 µM | 0.48 µM |

Figure 7

PL715 : Boc-βAla-Ala-Ala-Pro-Val-cmk
PL718: DOTA-βAla-Ala-Ala-Pro-Val-cmk

| Compound | Leukocyte elastase | Thrombin | tPA |
|---|---|---|---|
| PL715 | 77.2 nM | IC50>$10^{-5}$M | No inhibition |
| PL 718 | 16.4 nM | IC50>$10^{-5}$M | IC50 > $10^{-4}$M |

Figure 8

AGENTS FOR THE MOLECULAR IMAGING OF SERINE-PROTEASE IN HUMAN PATHOLOGIES

FIELD OF THE INVENTION

The present invention is directed to the use of irreversible ligands of the serine proteases, leukocyte elastase, thrombin, tissue plasminogen activator (t-PA) and plasmin, for the molecular imaging of said serine proteases in pathophysiological conditions associated with said serine protease activities.

BACKGROUND OF THE INVENTION

Serine proteases have been shown to play a role in diverse physiological functions, many of which can play important roles in disease processes such as cardiovascular disease (Kohler, H. T., et al., (2000) N. Engl. J. Med. 342(24):1792-801; Hamsten, A., et al., (2000) Thromb. Haemost. 83(3): 397403; Califf, R. M., et al., (2000) Circulation, 101(19): 2231-8; Krendel, S., et al., (2000) Ann. Emerg. Med. 35(5): 502-5), cancer (Schmidt, M., et al., (1999) Acta Otolaryngol. 119(8):949-53; Raigoso, P., et al., (2000) Int. J. Biol. Markers, 15(1):44-50; Haese, A., et al., (2000) J. Urol. 163(5): 1491-7; Hoopera, J. D., et al., (2000) Biochim. Biophys. Acta, 2000, 1492(1):63-71; Wallrapp, C., et al., (2000) Cancer Res. 2000, 60(10):2602-6; Cao, Y., et al., (2000) Int. J. Mol. Med. 2000, 5(5):547-51), asthma, chronic obstructive pulmonary disease (COPD), inflammatory diseases (Rice, K. D., et al., (1998) Curr. Pharm. Des., (5):381-96; Nadel, J. A., et al., (1998) Eur. Respir. J., (6):1250-1; Wright, C. D., et al., (1999) Biochem. Pharmacol., 58(12):1989-96; Burgess, L. E., et al., (1999) Proc. Natl. Acad. Sci. U.S.A., 96(15):8348-52; Barnes, P. J., et al., (2000) Chest, 117(2 Suppl):1OS-4S) and bacterial infections (Al-Hasani, K., et al., (2000) Infect. Immun., 68(5):2457-63; Gaillot, O., et al., (2000) Mol Microbiol. 35(6):1286-94; Lejal, N., et al., (2000) J. Gen. Virol., 81(Pt 4):983-92).

Accordingly, serine protease activities of leukocyte elastase, thrombin, tissue plasminogen activator (t-PA) and plasmin are considered as potential useful markers for the diagnosis of some of these pathologies. For example, the tissue pathology of serine proteases is linked to their ability to be retained within diseased tissue, therefore providing molecular targets for in situ molecular imaging. However there remains a need in the art for new approaches of the molecular imaging of serine proteases in tissues. Serine protease molecular imaging agents that are easy and relatively cheap to produce are therefore particularly desirable.

Leukocyte elastase, thrombin, tissue plasminogen activator (t-PA) and plasmin belong to the S1 family of serine proteases, whose the mechanism of action is well known (Barrett, Handbook of Proteolytic Enzymes, $2^{nd}$ Ed). The catalytic activity of the S1 family of proteases is provided by a charge relay system involving an aspartic acid residue that is hydrogen-bonded to a histidine, which itself is hydrogen-bonded to a serine. The sequences in the vicinity of the active site serine and histidine residues are well conserved in this family of proteases. The specificity of these proteases is essentially ensured by the "nonprime" domain of their active site i.e. the S5 or S4 to S1 binding subsites (following the nomenclature of Schechter and Berger (Schechter I., and Berger A. (1967) *Biochem Biophys Res Commun* 27, 157-162)) In these serine proteases, the amino acid interacting with the S1 subsite is either an arginine residue (t-Pa, Thrombin, Plasmin) or an hydrophobic residue (Leukocyte elastase)

Various irreversible ligands of the selected serine proteases are reported in the literature (Teger-Nilsson, 1977), (Kettner, 1978) (see table 1), They are constituted by small peptides interacting with the S5 or S4-S2 domain of the peptidase, and the amino acid binding the S1 subsite is replaced by an aminoacyl chloromethylketone (cmk) which interacts covalently with the serine of the catalytic site. Consequently, due to the restricted selectivity of the P1 residue, some of these irreversible inhibitors do not possess the required parameters of affinity and selectivity needed for a specific labelling of each protease. For example: in table 1, it was observed that the same peptide is described for Thrombin and t-PA.

TABLE 1

Examples of irreversible ligands of the selected serine proteases

| Serine protease | Peptide | Reference |
|---|---|---|
| Leukocyte elastase | MeOSucAla-Ala-Pro-Ala-cmk | Navia, PNAS, (1989), 86 |
| | MeOSucAla-Ala-Pro-Val-cmk | Powers, Biochim Biophys Acta (1977), 485, 156 |
| tPA | D-Phe-Pro-Arg-cmk | Boatman, J Med Chem (1999), 42, 1367 |
| Plasmin | D-Val-Phe-Lys-cmk | Woessner, Steroids (1989), 54, 491 |
| Thrombin | D-Phe-Pro-Arg-cmk | Kettner, Thromb Res (1979), 14, 969 |

However, as shown in table 1, the ligand D-Val-Phe-Lys-$COCH_2Cl$ (dVFK-cmk, M.W. 500) was developed as a very selective irreversible peptide ligand of plasmin active site with high affinity (Collen, Biochimica and Biophysica Acta, 165 (1980), 158-166).

Moreover, no investigations have been carried out to use these irreversible ligands for the molecular imaging of serine proteases.

SUMMARY OF THE INVENTION

The present invention relates to the development of molecular imaging agents that comprise one irreversible chloromethylketone (cmk) peptide ligand of a serine protease selected from the group consisting of leukocyte elastase, thrombin, tissue plasminogen activator (t-PA) and plasmin associated with one detectable moiety.

DETAILED DESCRIPTION OF THE INVENTION

The present invention is directed to the use of an irreversible ligand of a serine protease selected from the group consisting of leukocyte elastase, thrombin, tissue plasminogen activator (t-PA) and plasmin for the molecular imaging of said serine protease and the diagnosis of pathophysiological conditions associated with said serine protease activity. In particular, the invention encompasses molecular imaging agents, kits and strategies for specifically detecting the presence of said serine proteases using molecular imaging techniques.

The inventors have indeed demonstrated that peptide irreversible ligands of the selected serine proteases can be used for the molecular imaging of these serine proteases in physiological and physiopathological conditions by introducing at the N-terminal position of the irreversible cmk peptide ligand a detectable moiety (DOTA or DTPA) via a small spacer, in order to minimize a possible steric hindrance between these two moieties.

More particularly, they designed a derivative of D-Val-Phe-Lys-$COCH_2Cl$ (dVFK-cmk), substituted by a detectable moiety via a spacer, in order to study tissue plasmin in pathological conditions, by in vivo molecular imaging. They tested the ability of this new peptide to bind and inhibit plasmin in vitro, and demonstrated the ability of this peptide to target in vivo plasmin-rich tissues, by ($^{99m}$Tc) scintigraphy in several fibrinolytic-rich experimental models of cardiovascular pathologies in rats.

More particularly, they designed a derivative of an irreversible cmk peptide ligand of thrombin substituted by a detectable moiety via a spacer, in order to study tissue thrombin in pathological conditions. They tested the ability of this new peptide to bind and inhibit thrombin in vitro and in vivo.

They also designed a derivative of an irreversible cmk peptide ligand of leukocyte elastase substituted by a detectable moiety via a spacer, in order to study tissue leukocyte elastase in pathological conditions. They tested the ability of this new peptide to bind and inhibit leukocyte elastase in vitro and in vivo.

They also designed a derivative of an irreversible cmk peptide ligand of tissue plasminogen activator (tPA) substituted by a detectable moiety via a spacer, in order to study tPA in pathological conditions. They tested the ability of this new peptide to bind and inhibit tPA in vitro and in vivo.

Accordingly, the present invention relates to "serine protease-targeted molecular imaging agents" that comprise at least one irreversible peptide ligand of a serine protease associated with at least one detectable moiety, wherein said serine protease is selected from the group consisting of leukocyte elastase, thrombin, tissue plasminogen activator (t-PA) and plasmin.

As used herein, the term "molecular imaging agent" refers to a compound that can be used to detect specific biological elements (e.g., biomolecules) using molecular imaging techniques. Molecular imaging agents of the present invention can be used to detect the serine protease of interest in tissues of a subject.

The term "irreversible peptide ligand of a serine protease" or "irreversible chloromethylketone (cmk) peptide ligand of a serine protease" refers to any modified peptide that is capable to form a covalent complex with the essential amino acid serine of the catalytic triad of the serine protease. According to the invention the irreversible ligands of the selected serine proteases have to exhibit high affinity, specificity and/or selectivity for said serine proteases.

In one embodiment, the present invention relates to a leukocyte elastase-targeted molecular imaging agent that comprise at least one irreversible peptide ligand of leukocyte elastase associated with at least one detectable moiety wherein said irreversible peptide ligand has the general formula (I):

P—X—Y—Z-Pro-Val-cmk    (I)

wherein:
P represents a protective group such as Acetyl (Ac), tButyloxycarbonyl (Boc)
X represents Gly, Ala or β-Ala
Y represents Gly, Ala or Leu
Z represents Ala, Val, Ile, or Leu.
In formula (I), when Y and Z are chiral amino acids then could be under the L or D configuration Accordingly the present invention relates to a tPA-targeted molecular imaging agent that comprise at least one irreversible peptide ligand of tPA associated with at least one detectable moiety wherein said irreversible peptide ligand has the general formula II:

P—X1-Pro-Y1-Gly-Arg-cmk    (II)

wherein:
P represents a protective group such as Acetyl (Ac), tButyloxycarbonyl (Boc)
X1 represents Gly or Ala
Y1 represents Phe, Tyr, Ile or Leu
In formula (II), when X1 and Y1 are chiral amino acids, they could be under the L or D configuration.

Accordingly the present invention relates to a thrombin-targeted molecular imaging agent that comprise at least one irreversible peptide ligand of thrombin associated with at least one detectable moiety wherein said irreversible peptide ligand has the general formula II:

P—X2-Y2-Z2-Arg-cmk    (III)

wherein:
P represents a protective group such as Acetyl (Ac), tButyloxycarbonyl (Boc)
X2 represents Gly or βAla
Y2 represents Phe, Val, Ile or Leu
Z2 represents Pro or Gly
In formula (III), when X2, Y2 and Z2 are chiral amino acids; they could be under the L or D configuration.

Accordingly the present invention relates to a plasmin-targeted molecular imaging agent that comprise at least one irreversible peptide ligand of plasmin associated with at least one detectable moiety wherein said irreversible peptide ligand is D-Val-Phe-Lys-cmk.

The term "detectable moiety", as used herein refers to any entity which, when part of a molecule, allows visualization of the molecule by using molecular imaging techniques. In the context of the present invention, detectable moieties are entities that are detectable by molecular imaging techniques such as Magnetic Resonance Imaging (MRI), planar scintigraphy (PS), Positron Emission Tomography (PET), Single Photon Emission Computed Tomography (SPECT), or any combination of these techniques. Preferably, detectable moieties are stable, non-toxic entities which, when part of a serine protease-targeted molecular imaging agent, retain their properties under in vitro and in vivo conditions.

In certain embodiments, the serine protease-targeted molecular imaging agent is designed to be detectable by a nuclear medicine molecular imaging techniques such as planar scintigraphy (PS), Positron Emission Tomography (PET) and Single Photon Emission Computed Tomography (SPECT). In such embodiments, the molecular imaging agent of the invention comprises at least one irreversible inhibitor of the selected serine protease associated with at least one radionuclide (i.e., a radioactive isotope).

SPECT and PET acquire information on the concentration of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Planar scintigraphy (PS) is similar to SPECT in that it uses the same radionuclides. However, PS only generates 2D-information.

Thus, in certain embodiments, the detectable moiety in a molecular imaging agent of the invention is a radionuclide detectable by PET such as Gallium-68 (68Ga).

In other embodiments, the detectable moiety is a radionuclide detectable by planar scintigraphy or SPECT. Examples of such radionuclides include technetium-99m (99mTc), gallium-67 (67Ga), yttrium-91 (91Y), indium-111 (111In), rhenium-186 (186Re), and thallium-201 (201Tl). Preferably, the radionuclide is technetium-99m (99mTc). Over 85% of the routine nuclear medicine procedures that are currently performed use radiopharmaceutical methodologies based on 99mTc.

In certain embodiments, the serine protease-targeted molecular imaging agent is designed to be detectable by Magnetic Resonance Imaging (MRI). MRI has the advantage (over other high-quality molecular imaging methods) of not relying on potentially harmful ionizing radiation. Thus, in certain embodiments, the molecular imaging agent of the invention comprises at least one irreversible inhibitor of the serine protease associated with at least one paramagnetic metal ion. Example of paramagnetic metal ions detectable by MRI is gadolinium III ($Gd^{3+}$), which is an FDA-approved contrast agent for MRI, or iron oxide, which gives a sensitive negative signal in MRI.

The inventive molecular imaging agents may be prepared by any synthetic method known in the art, the only requirement being that, after reaction, the irreversible inhibitor of the serine protease and detectable moiety retain their affinity and detectability property, respectively. The irreversible ligands of the serine protease and detectable moieties may be associated in any of a large variety of ways. However, the detectable moiety being a metal entity, the irreversible inhibitor of the serine protease is associated to the detectable metal entity via a metal-chelating moiety. The irreversible inhibitor of the serine protease is associated to the metal-chelating moiety by a covalent bond through a small spacer. Accordingly the N-terminal protective group (P) of the "irreversible inhibitor" of thrombin, tPA or Leukocyte Elastase as described in formula (I), (II) or (III), is replaced by the selected spacer before the association with the metal chelating moiety.

The small spacer is either a Gly residue or the benzylthiourea generated by the introduction of the commercially available metal-chelating moiety (p-SCN-Bn-DOTA, p-SCN-Bn-DTPA or p-SCN-Bn-NOTA).

Suitable metal-chelating moieties for use in the present invention may be any of a large number of metal ligands and metal complexing molecules known to bind detectable metal moieties. Preferably, metal-chelating moieties are stable, non-toxic entities that bind radionuclides or paramagnetic metal ions with high affinity.

Examples of metal-chelating moieties that have been used for the complexation of paramagnetic metal ions, such as gadolinium III ($Gd^{3-}$), include DTPA (diethylene triaminepentaacetic acid); DOTA (1,4,7,10-tetraazacyclododecane-N,N',N'',N'''-tetraacetic acid); and derivatives thereof (see, for example, U.S. Pat. Nos. 4,885,363; 5,087,440; 5,155,215; 5,188,816; 5,219,553; 5,262,532; and 5,358,704; and D. Meyer et al., Invest. Radiol. 1990, 25: S53-55), in particular, DTPA-bis(amide) derivatives (U.S. Pat. No. 4,687,659). Other ligands also include NOTA (1,4,7-triaza-cyclononane N,N',N''-triacetic acid), and HYNIC (6-Hydrazinopyridine-3-carboxylic acid).

The invention provides reagents and strategies to image the presence of the serine proteases of interest in tissues. More specifically, the invention provides targeted reagents that are detectable by molecular imaging techniques and methods that allow the detection, localization and/or quantification of serine proteases in living subjects, including human patients.

As used herein, the term "subject" refers to a human or another mammal (e.g., mouse, rat, rabbit, hamster, dog, cat, cattle, swine, sheep, horse or primate). In many embodiments, the subject is a human being. In such embodiments, the subject is often referred to as an "individual" or a "patient if the subject is afflicted with a disease or clinical condition. The terms "subject", "individual" and "patient" do not denote a particular age, and thus encompass adults, children and newborns.

More specifically, the present invention provides methods for detecting the presence of the selected serine protease (i.e. leukocyte elastase, thrombin, tissue plasminogen activator (t-PA) and plasmin) in a tissue's patient. The methods comprise administering to the patient an effective amount of a serine protease-targeted molecular imaging agent of the invention, or a pharmaceutical composition thereof. The administration is preferably carried out under conditions that allow the molecular imaging agent (1) to reach the tissue(s)'s patient that may contain abnormal serine proteases (i.e., serine proteases associated with a clinical condition) and (2) to interact with such serine proteases so that the interaction results in the binding of the molecular imaging agent to the serine proteases. After administration of the serine protease-targeted molecular imaging agent and after sufficient time has elapsed for the interaction to take place, the molecular imaging agent bound to serine proteases present in the patient is detected by a molecular imaging technique. One or more images of at least part of the body of the patient may be generated.

Administration of the serine protease-targeted molecular imaging agent, or pharmaceutical composition thereof, can be carried out by any suitable method known in the art such as administration by oral and parenteral methods, including intravenous, intraarterial, intrathecal, intradermal and intracavitory administrations, and enteral methods.

Accordingly, the molecular imaging agents of the invention represent powerful tools for the diagnosis of pathological conditions that are associated with serine proteases selected from the group consisting of leukocyte elastase, thrombin, tissue plasminogen activator (t-PA) and plasmin.

The terms "pathological condition associated with serine proteases", "disease associated with serine proteases" and "disorder associated with serine proteases" are used herein interchangeably. They refer to any disease condition characterized by undesirable or abnormal tissue serine protease activity. Such conditions may result from a tissue degeneration mediated by the serine proteases selected from the group consisting of leukocyte elastase, thrombin, tissue plasminogen activator (t-PA) and plasmin. The term include for example, disease conditions associated with or resulting from the homing of leukocytes to sites of pathologies the interaction of platelets with activated endothelium, platelet-platelet and platelet-leukocyte interactions in the blood vascular compartment, the formation of intraluminal or intraparietal thrombi, and the like. The term also includes all tissue degenerative pathologies involve less or more serine protease activation, including plasmin formation, t-PA, thrombin and/or leukocyte protease release and retention. For example these human pathologies include all forms of atherothrombotic diseases whatever the localisation (coronary artery diseases, cerebrovascular disease including stroke, aneurysms of the aorta, leg ulcers, etc.), acute and chronic pulmonary pathologies, including Acute Respiratory Distress Syndrome, emphysema and Chronic Obstructive Pulmonary Disease (COPD), arthritis, auto-immune diseases, certain forms of localized infectious diseases. The term also includes cancers.

The diagnosis is thus achieved by examining and molecular imaging parts of or the whole body of the patient. Comparison of the results obtained from the patient with data from studies of clinically healthy individuals will allow determination and confirmation of the diagnosis.

These methods can also be used to follow the progression of a pathological condition associated with serine proteases selected from the group consisting of leukocyte elastase, tissue plasminogen activator (t-PA) and plasmin. For example, this can be achieved by repeating the method over a period of time in order to establish a time course for the presence, localization, distribution, and quantification of "abnormal" serine proteases in a patient's tissue.

These methods can also be used to monitor the response of a patient to a treatment for a pathological condition associated with serine proteases selected from the group consisting of leukocyte elastase, thrombin, tissue plasminogen activator (t-PA) and plasmin. For example, an image of part of the patient's body that contains tissue "abnormal" serine proteases is generated before and after submitting the patient to a treatment. Comparison of the "before" and "after" images allows the response of the patient to that particular treatment to be monitored.

In the methods of molecular imaging of serine proteases and of diagnosis of pathological conditions associated with serine proteases described herein, the molecular imaging agents of the present invention may be used per se or as a pharmaceutical composition.

Accordingly, in one aspect, the present invention provides for the use of irreversible ligands of serine protease for the manufacture of a composition for the diagnosis of clinical conditions associated with serine proteases selected from the group consisting of leukocyte elastase, thrombin, tissue plasminogen activator (t-PA) and plasmin.

In another aspect, the present invention provides pharmaceutical compositions comprising at least one serine protease-targeted molecular imaging agent and at least one pharmaceutically acceptable carrier.

As used herein, the term "pharmaceutically acceptable carrier" refers to a carrier medium which does not interfere with the effectiveness of the biological activity of the active ingredients and which is not excessively toxic to the hosts at the concentrations at which it is administered. The term includes solvents, dispersion media, coatings, antibacterial and antifungal agents, isotonic agents, adsorption delaying agents, and the like. The use of such media and agents for pharmaceutically active substances is well known in the art (see for example, Remington's Pharmaceutical Sciences, E. W. Martin, 18th Ed., 1990, Mack Publishing Co., Easton, Pa.).

Pharmaceutical compositions will be administered by injection. For administration by injection, pharmaceutical compositions of molecular imaging agents may be formulated as sterile aqueous or non-aqueous solutions or alternatively as sterile powders for the extemporaneous preparation of sterile injectable solutions. Such pharmaceutical compositions should be stable under the conditions of manufacture and storage, and must be preserved against the contaminating action of microorganisms such as bacteria and fungi.

Pharmaceutically acceptable carriers for administration by injection are solvents or dispersion media such as aqueous solutions (e.g., Hank's solution, alcoholic/aqueous solutions, or saline solutions), and non-aqueous carriers (e.g., propylene glycol, polyethylene glycol, vegetable oil and injectable organic esters such as ethyl oleate). Injectable pharmaceutical compositions may also contain parenteral vehicles (such as sodium chloride and Ringer's dextrose), and/or intravenous vehicles (such as fluid and nutrient replenishers); as well as other conventional, pharmaceutically acceptable, non-toxic excipients and additives including salts, buffers, and preservatives such as antibacterial and antifungal agents (e.g., parabens, chlorobutanol, phenol, sorbic acid, thirmerosal, and the like). Prolonged absorption of the injectable compositions can be brought about by adding agents that can delay absorption (e.g., aluminum monostearate and gelatin). The pH and concentration of the various components can readily be determined by those skilled in the art.

Sterile injectable solutions are prepared by incorporating the active compound(s) and other ingredients in the required amount of an appropriate solvent, and then by sterilizing the resulting mixture, for example, by filtration or irradiation.

In general, the dosage of a serine protease-targeted molecular imaging agent (or pharmaceutical composition thereof) will vary depending on considerations such as age, sex and weight of the patient, as well as the particular pathological condition suspected to affect the patient, the extent of the disease, the tissue(s) of the body to be examined, and the sensitivity of the detectable moiety. Factors such as contraindications, therapies, and other variables are also to be taken into account to adjust the dosage of molecular imaging agent to be administered. This, however, can be readily achieved by a trained physician.

In general, a suitable daily dose of a serine protease-targeted molecular imaging agent (or pharmaceutical composition thereof) corresponds to the lowest amount of molecular imaging agent (or pharmaceutical composition) that is sufficient to allow molecular imaging of any relevant (i.e., generally overexpressed) serine protease present in the patient. To minimize this dose, it is preferred that administration be intravenous, intramuscular, intraperitoneal or subcutaneous, and preferably proximal to the site to be examined. For example, intravenous administration is appropriate for molecular imaging the cardio/neurovascular system; while intraspinal administration is better suited for molecular imaging of the brain and central nervous system.

In another aspect, the present invention provides kits comprising materials useful for carrying out the diagnostic methods of the invention. The diagnostic procedures described herein may be performed by clinical laboratories, experimental laboratories, or practitioners.

In certain embodiments, an inventive kit comprises at least one irreversible ligands of serine protease as above described and at least one detectable entity, and, optionally, instructions for associating the irreversible ligands of serine protease and detectable entity to form a serine protease-targeted molecular imaging agent according to the invention. The detectable entity is preferably a short-lived radionuclide such as technetium-99m (99mTc), gallium-67 (67Ga), yttrium-91 (91Y), indium-111 (111In), rhenium-186 (186Re), and thallium-201 (201Tl). Preferably, the irreversible ligands of serine protease and detectable entity are present, in the kit, in amounts that are sufficient to prepare a quantity of molecular imaging agent that is suitable for the detection of serine proteases and diagnosis of a particular clinical condition in a subject.

In addition, the kit may further comprise one or more of: labelling buffer and/or reagent; purification buffer, reagent and/or means; injection medium and/or reagents. Protocols for using these buffers, reagents and means for performing different steps of the preparation procedure and/or administration may be included in the kit.

The different components included in an inventive kit may be supplied in a solid (e.g., lyophilized) or liquid form. The kits of the present invention may optionally comprise different containers (e.g., vial, ampoule, test tube, flask or bottle) for each individual component. Each component will generally be suitable as aliquoted in its respective container or provided in a concentrated form. Other containers suitable for conducting certain steps of the preparation methods may also be provided. The individual containers of the kit are preferably maintained in close confinement for commercial sale.

In certain embodiments, a kit further comprises instructions for using its components for the diagnosis of clinical conditions associated with serine proteases according to a method of the present invention. Instructions for using the kit according to a method of the invention may comprise instructions for preparing a molecular imaging agent from the irreversible ligands of serine protease and detectable entity, instructions concerning dosage and mode of administration of the molecular imaging agent obtained, instructions for performing the detection of serine proteases, and/or instructions for interpreting the results obtained. A kit may also contain a notice in the form prescribed by a governmental agency regulating the manufacture, use or sale of pharmaceuticals or biological products.

The invention will be further illustrated by the following figures and examples. However, these examples and figures should not be interpreted in any way as limiting the scope of the present invention.

EXAMPLE 1

Design of a Peptide Ligand for Plasmin Molecular Imaging

Plasmin catalyses the cleavage of Lys-X or Arg-X bonds with specificity similar to that of trypsin, but with a lesser efficiency for hydrolysis of these bonds in proteins. In this family of proteases the selectivity of the enzyme is essentially ensured by the amino acid interacting with the S1 subsite and, consequently plasmin is able to cleave esters or amides of Lys and Arg as well as small peptide substrate recognizing the S3 to S1 subsites of the enzyme and containing a C-terminal lysine or arginine {Lottenberg, 1981}. Likewise, small three amino acids peptide analogues, such as leupeptin (Ac-Leu-Leu-Arg-H), are efficient competitive inhibitors with Ki values in the $10^{-7}$ molar range {Chi, 1989}.

Figure 1:
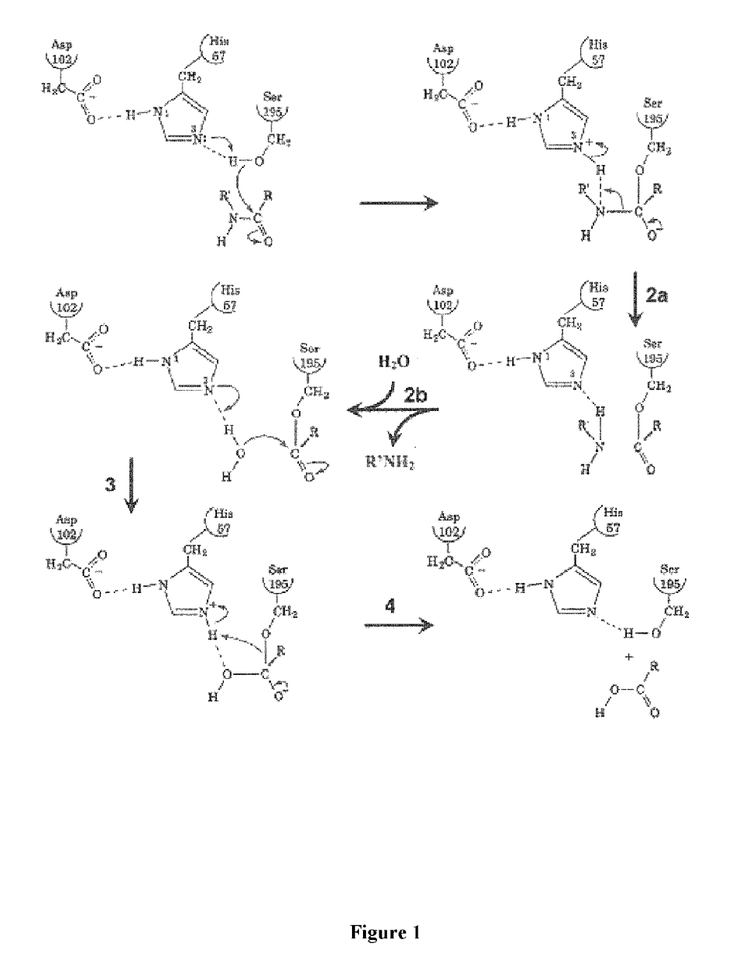
FIG. 1 shows the main player in the catalytic mechanism of serine protease is the "catalytic triad".
Figure 2:
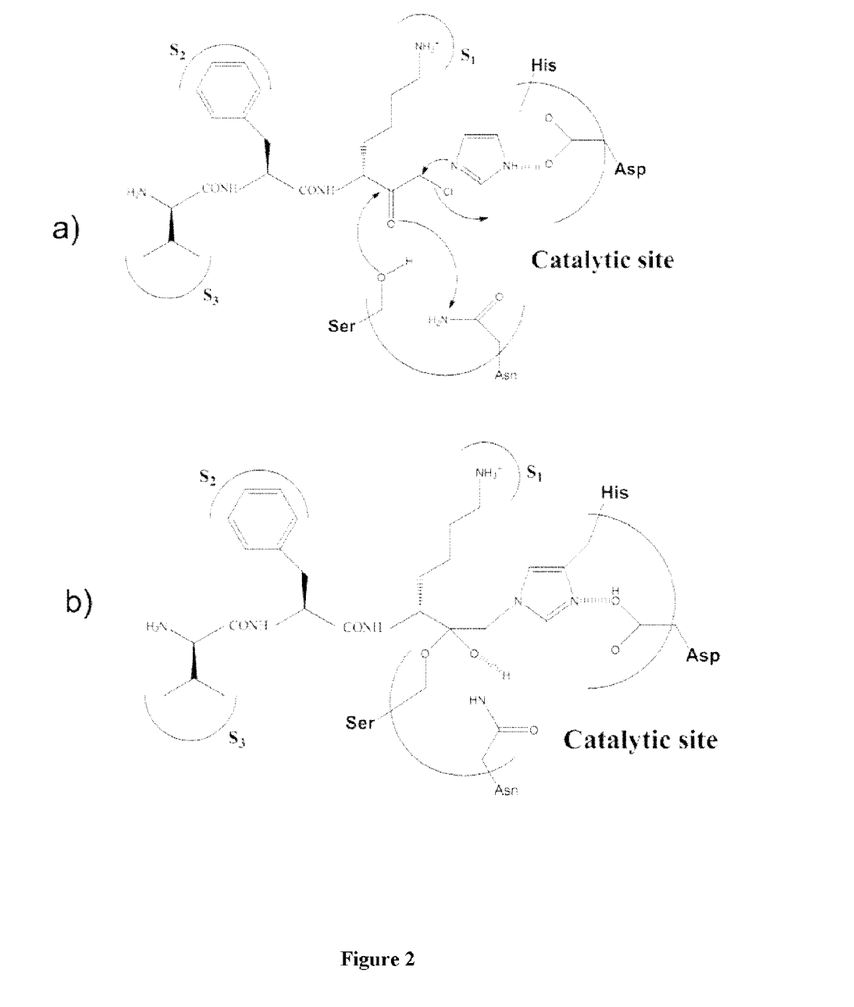
FIG. 2 shows the schematic representation of a proposed mechanism of Plasmin by DVal-Phe-Lys-cmk: a) Michaelis complex; b) final alkylated product.

However, to obtain an efficient labeling of the peptidase for molecular imaging, an irreversible inhibitor has been chosen as starting material for the design of such a marker. Indeed, the replacement of the C-terminal carboxylate of Lys, by a chloro methyl ketone CO—$CH_2$—Cl in the three amino acids peptide D-Val-Phe-Lys, allowed the irreversible inhibition of plasmin by formation of a covalent complex between the inhibitor and essential amino acids (His and Ser) of the catalytic site, as shown in FIG. 2a, b.

Using this peptide as model, we decided to introduce the metal chelating agent, DOTA or DTPA in N-terminal position via a small spacer (Gly) in order to minimize the steric hindrance due to the large size of the ligand.

Moreover, due to the covalent nature of these inhibitors, the possible presence of an important non specifique binding has to be considered. For this purpose, an analogue of dV-F—K-cmk, without affinity for plasmin, dV-F-A-cmk or DOTA dV-F-A-cmk, has been prepared and used to determine the "background noise".

DOTA is more specific for the complexation of Ga or Gd cation whereas DTPA is use for the complexation of Tc.

Synthetic Pathway:

Synthesis of the Aminoacyl Chloromethylketone

The carboxylate group of the N-protected amino acid, Boc-Lys(εN—Z)—OH or Boc-Ala-OH is transformed into a mixed anhydride by action of i-Bu-chloroformate in presence of N-methylmorpholine, then the addition of diazomethane CH$_2$N$_2$, formed the corresponding diazoketone. Treatment by saturated HCl in Dioxanne solution gives the chloromethylketone and the deprotection of the amine function is performed by action of TFA in CH$_2$Cl$_2$.

Synthesis of the N-Protected Tripeptide Boc-Gly-dVal-Phe

The peptide is synthesized by liquid phase method using EDCI, HOBT or TBTU as coupling reagents in four steps: i) synthesis of Boc-dVal-Phe-OCH$_3$, ii) deprotection of the amine group by TFA/CH$_2$Cl$_2$, iii) Coupling of Boc-Gly to H-dVal-Phe-OCH$_3$, iv) saponification of the methyl ester leading to Boc-Gly-dVal-Phe.

Synthesis of the Final Marker

-continued

The tripeptide Boc-Gly-dVal-Phe is coupled with the chloromethylketone, Lys (εN—Z)-cmk or Ala-cmk by the mixed anhydride method and the Boc-group eliminated and replaced by the DOTA group, using DOTA-NHS with DIEA in DMF, or by the DTPA group, using DTPA di-anhydride DMSO/Hepes buffer.

For peptides containing a lysine residue, the last step corresponds to the deprotection of the ε-amino group by HBr in AcOH.

The different inhibitors synthesized are summarized below:
dVFK-cmk
PL700: G-dV-F—K-cmk
PL701: DOTA-G-dV-F—K-cmk
PL702: G-dV-F-A-cmk
PL703: DOTA-G-dV-F-A-cmk
PL704: DTPA-G-dV-F—K-cmk

EXAMPLE 2

In Vitro Ligation of the Plasmin Active Site by PL704

Material and Methods:
Determination of Plasmin Activity:
10 nM of plasmin from human plasma (calbiochem) was diluted in Tris-HCl buffer pH 7.4 50 mM, NaCl 100 mM and Tween-20 0.01%. The samples were then incubated or not with the different inhibitors (see below) for 15 minutes at room temperature. Then, the fluorescent substrate (Suc-Ala-Phe-Lys-AMC, 40 mM) was added just before reading ($\lambda$ excitation 390 nm, $\lambda$ emission 460 nm) on the Fluoroskan Ascent plate reader (Thermo Fisher). The fluorescence intensity was evaluated every 10 minutes for 2 hours at 37° C.—The integration time for each measure was 20 ms.

Each inhibitor was tested in a range of concentrations from 5 nM up to 1000 nM. All the inhibitors were tested in duplicates for each concentration and 4 independent experiments were performed.

Statistical Analysis:
Results are presented as % of active plasmin. The differences between the concentrations of each inhibitor were evaluated by paired t-test using StatView software. Statistical significance was accepted when p<0.05.

Figure 3:
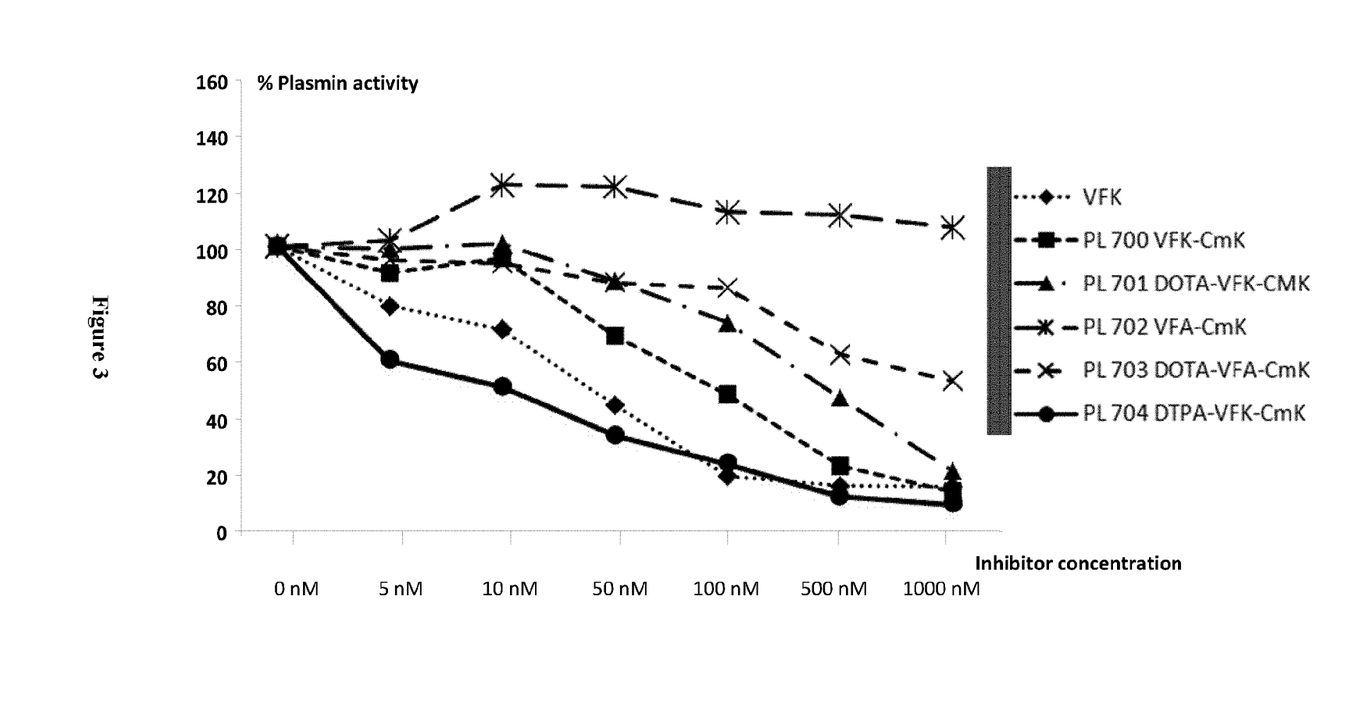
FIG. 3 shows the plasmin inhibition of VFK, PL702, PL700, PL703, PL701 and PL704: the dose-dependant inhibitory capacity of each molecule (n=4) was evaluated in the presence of 10 nM of plasmin. Plasmin with or without inhibitors was incubated at room temperature for 15 min. The fluorescent substrate (40 μM) was added just before reading (λ excitation 390 nM, λ emission 460 nM)

Results:
As expected, we observed a significant dose-dependent effect of dV-F—K and PL 700 (G-dV-F—K-cmk) on plasmin activity from 5 nM (p=0.0038 vs control). When lysine residue is replaced by alanine (PL702), the inhibitory effect is totally abolished. However, adding of a DOTA group on PL702, corresponding to PL703, induced an inhibition of plasmin activity which is not significant until 1000 nM. The PL704 (DTPA-G-dV-F—K-cmk) inhibitor induced a significant dose dependant inhibition of plasmin activity from 5 nM (p=0.0385 vs control). As compared to dV-F—K, the plasmin inhibition by PL704 at low concentrations is higher but the difference is not significant. PL701 (DOTA-G-dV-F—K-cmk) also induced a dose dependant inhibition of plasmin activity which is significant from 50 nM (p=0.016 vs control) (FIG. 3).

The table 4 gives the mean and the standard deviation of % of plasmin activity for all inhibitors

TABLE 4

| | | 0 nM | 5 nM | 10 nM | 50 nM | 100 nM | 500 nM | 1000 nM |
|---|---|---|---|---|---|---|---|---|
| VFK | Mean | 100.0 | 77.1 | 68.3 | 39.1 | 11.9 | 8.0 | 7.8 |
| | SEM | 0.0 | 4.1 | 18.4 | 12.5 | 2.8 | 0.3 | 0.4 |
| PL 700 VFK-CmK | Mean | 100.0 | 89.8 | 95.6 | 65.7 | 43.1 | 15.8 | 5.8 |
| | SEM | 0.0 | 5.2 | 15.0 | 9.2 | 8.0 | 8.1 | 4.1 |
| PL 701-VFK-CmK-DOTA | Mean | 100.0 | 83.0 | 79.1 | 68.7 | 54.6 | 34.1 | 12.8 |
| | SEM | 0.0 | 6.7 | 17.9 | 15.9 | 13.5 | 5.3 | 3.0 |
| PL 702 VFA-CmK | Mean | 100.0 | 102.3 | 123.5 | 122.9 | 113.3 | 112.1 | 107.3 |
| | SEM | 0.0 | 5.2 | 11.0 | 11.4 | 6.4 | 5.1 | 6.2 |
| PL 703 VFA-CmK-DOTA | Mean | 100.0 | 94.9 | 93.6 | 86.1 | 84.1 | 58.4 | 48.4 |
| | SEM | 0.0 | 7.6 | 18.3 | 23.9 | 20.6 | 23.7 | 19.1 |
| PL 704 VFK-CmK-DTPA | Mean | 100.0 | 56.3 | 46.2 | 27.4 | 16.6 | 4.0 | 1.1 |
| | SEM | 0.0 | 13.2 | 7.0 | 0.9 | 2.5 | 1.0 | 0.5 |

EXAMPLE 3

Ex Vivo and In Vivo Scintigraphy

Material and Methods:

Experimental Models:

we have used several experimental models of endovascular thrombus formation in rats, which have been already developed for molecular molecular imaging of platelet activation and fibrin formation, including aneurysm of the abdominal aorta {Sarda-Mantel, 2006}, endocarditic vegetations {Rouzet, 2008}. Aneurysm of the aorta was induced by matrix decellularized xenograft in rats {Allaire, 1996}, and endocarditis by left or right ventricle catheterization followed by provoked bacteraemia {Rouzet, 2008} as previously described. These thrombus models were completed by a model of stroke, provoked by cerebral autologous thrombus emboli in rats (reference).

These experimental models were also compared to 99m Tc aprotinin signal ex vivo on human aneurymal thrombus.

Radiolabelling Procedures:

Aprotinin Labelling with $^{99m}$Technetium:

Aprotinin labelling was performed according to a procedure modified from Schaadt et al. (J Nucl Med 2003; 44: 177-183).

DOTA-G-dVFKcmk, DOTA-G-dVFAcmk, and DTPA-G-dVFKcmk Labelling with $^{111}$Indium:

One hundred and eleven MBq of $^{111}$Indium chlorure (Mallinckrodt, France) were mixed with 10 μg of the tracer diluted in 80 μl of Ammonium Acetate buffer (0.1 M; pH 6.45), and allowed to incubate for 1 hour at 40° C. The quality control was performed with instant thin-layer chromatography (ITLC-SG), using acetone as eluant. The radiolabeling yield was around 90%.

DTPA-G-dVFKcmk Labelling with $^{99m}$Technetium:

$^{99m}$Tc-sodium pertechnetate (740 MBq) freshly eluted was mixed with 10 μg of DTPA-G-dVFKcmk, 4 μl of stannous chloride, and 2 μl of potassium borohydrure, and allowed to incubate for 1 hour at 40° C. The quality control was performed with instant thin-layer chromatography (ITLC-SG), using acetone as eluant. The radiolabelling yield was around 90%.

Single Photon Emission Computed Tomography (SPECT):

SPECT Acquisitions:

All acquisitions were performed using a dedicated small animal γIMAGER-S system (Biospace Lab, France) equipped with parallel low-energy high resolution collimators, 256×256 matrix, 15% energy window centered on 140 keV. A dual-head SPECT acquisition was performed for 60 min associated with an helicoidal computed tomography scan (μCT, Biospace Lab, France) for image co-registration. Acquisitions were performed under intraperitoneal (rats) pentobarbital anaesthesia (40 mg/Kg b.w., Ceva Santé Animale, France), 2 hours after intravenous infusion of the radiotracer. Targeted activities were 111 MBq (range 62.9-150.6) for $^{99m}$Tc and 28 MBq (range 25.9-37) for $^{111}$In.

Processing:

After completion of acquisitions, raw CT data were converted into 256 axial slices using the dedicated Biospace software, then reformatted into DICOM. Raw SPECT data were reformatted into DICOM, then transferred on a Xeleris 2 workstation (GE Medical Systems, Buc, France) and reconstructed in a 128×128 matrix, using OSEM (2 iterations, 8 subsets) with Butterworth 3D post-filtering (cut-off frequency 1.33 cycle/pixel, order 10).

Quantitative Analysis:

Fused images of both SPECT and CT were displayed for co-registration. A focal uptake of the radiotracer in the relevant area (heart, abdominal aorta, or brain according to the model) was assessed visually, and its intensity was quantified using the target to background ratio. For that purpose, a region of interest was manually drawn over the focal uptake to quantify its activity (counts/min/mm$^2$). The background activity was determined by a second region of interest drawn over the lungs (endocarditis model), the supra-renal aorta (AAA model), or the contralateral brain hemisphere (stroke model).

Binding in Excised Human AAA Samples:

Aneurysm thrombi (of 5 mm thickness) obtained from 2 patients who undergone surgical AAA resection were incubated with either $^{99m}$Tc-aprotinin or $^{99m}$TcDTPA-G-dVFKcmk—diluted in RPMI-1640 medium (volumetric activity: 2 MBq/ml) for 30 min at room temperature. After incubation, the thrombus slices were rinsed 5 times with ice-cold RPMI-1640 medium. Then a 30 min scintigraphic planar acquisition (Biospace Lab, France) was performed to assess the global uptake of the tracer. After freezing, samples were cut into 20 μm transverse sections for autoradiography. Activity (counts/mm$^2$) were measured on autoradiograms {Petegnief, 1998} by drawing regions of interest on each layer of the thrombus (luminal, intermediate and abluminal), and were corrected from the background activity. Activity ratios between $^{99m}$Tc-aprotinin and $^{99m}$Tc-albumin were calculated for each layer.

Quantitative Autoradiography:

Relevant tissues (heart, abdominal aorta, or brain according to the model) were carefully dissected, frozen and cut into transverse sections of 20 μm thickness, which were exposed in a digital radioimager (Instant Imager, Packard, Meriden, USA) for 12 hours. The activity normalized to the region of interest area (mean counts/min/mm$^2$ corrected for background activity) was determined on autoradiograms. Quantification was performed by calculating the ratio between the activity of the relevant tissue and the activity of a region of interest drawn on either normal myocardium remote from the vegetation in the endocarditis model, supra-renal aorta sample in the AAA model, or the contralateral brain hemisphere in the stroke model. According to calibration studies previously reported, with activity standards of tissue-equivalent homogenates, 50 counts/min/mm$^2$ of $^{99m}$Tc-ANX approximated 210 kBq/mg in autoradiography {Petegnief, 1998}

Histology:

Some representative samples of left- and right-sided endocarditis vegetations in rabbits and rats, including aortic tissue, aortic valves, superior vena cava, right atria, tricuspid and pulmonary valves, and left and right ventricles were fixed in paraformaldehyde for 24 H, embedded in paraffin for morphological analysis, or frozen in OCT for cryostat sectioning and immunohistochemistry. Five-micrometer thick serial sections were routinely stained with Masson's trichrome to visualize erythrocytes and fibrin, hematoxylin/eosin for cells and nuclei, Alcian blue coupled with nuclear red {Scott, 1996} to reveal areas of mucoid accumulation and their relation to cell nuclei, orcein for elastin and Sirius Red for collagen.

Cryostat sections were used for autoradiography and then stained by Masson's trichrome, and the full sections were reconstituted under the microscope using Cartograph software (Microvision, France). Superposition of both images at the same scale was then processed (fusion images) in order to localize $^{99m}$Tc-ANX uptake (autoradiography) on histological sections.

Results:

Whatever the model used, (99mTc)DTPA-G-dVFKcmk, give a detectable signal related to the localized lesion, by in vivo SPECT and by autoradiographies. (99mTc)DTPA-G-dVFKcmk has a high in vivo uptake by bone marrow for which the specificity has not yet been explored.

Abdominal Aortic Aneurysm in Rats:

On SPECT acquisitions performed in vivo 2 hours after radiotracers injection, the AAA was detectable in n/N rats with 99mTc-DTPA-G-dVFKcmk and in none/N rats with 99mTc-Aprotinin. Autoradiography gave similar results with greater ratios with 99mTc-DTPA-G-dVFKcmk. Despite the high uptake intensity on autoradiography, the lack of detectability of AAA uptake in vivo is related to: (1) the small volume of the mural thrombus which is inferior to the spatial resolution of the detection system (#3 mm) thus generating a partial volume effect leading to an underestimation of the intensity of the uptake, and (2) the high background activity coming from the surrounding structures such as kidneys and bone marrow of the rachis (Table 5).

TABLE 5

| Radiolabelling SPECT | DTPA-G-dVFKcmk (n = 10) | Aprotinin (n = 10) | P value |
|---|---|---|---|
| Autoradiography | 7.57 ± 3.32 | 4.95 ± 0.90 | 0.027 |

Figure 4:
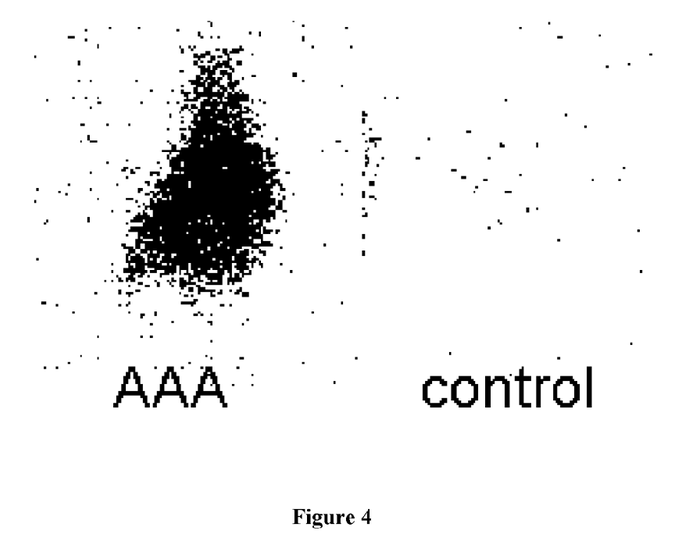
FIG. 4 shows ex vivo imaging of experimental aneurysm in rat.

In order to assess the specificity of the tracer uptake by the mural thrombus, we performed a pre-injection of 20 nmoles of non-labelled DTPA-G-dVFKcmk in 2 animals, followed 10 minutes later by the injection of 2 nmoles of radiolabelled DTPA-G-dVFK-cmk, which resulted in a fivefold decrease of the intensity of the uptake compared with animals without pre-injection of the non-labelled compound (quantified by autoradiography: 1.34±0.30 vs 7.57±3.32 cpm/mm$^2$ respectively, p=0.032 using Mann-Whitney U test) (FIG. 4).

Right-Sided Endocarditis in Rats:

On SPECT acquisitions performed in vivo 2 hours after radiotracers injection, the vegetation uptake was detected in n/N rats with 99mTc-DTPA-G-dVFKcmk and in none/N rats with 99mTc-Aprotinin.

Left-Sided Endocarditis in Rats:

In this model we compared the uptake of DTPA-G-dVFK-cmk with that of a non-specific analog (DOTA-G-dVFA-cmk) obtained by the substitution of Lysin by Alanin, labelled with $^{111}$Indium (Table 6).

TABLE 6

| SPECT | 99mTc-DTPA-G-dVFKcmk (n = 5) | 111In-DOTA-G-dVFAcmk (n = 6) | P value |
|---|---|---|---|
| Autoradiography | 10.65 ± 1.07 | 2.66 ± 0.47 | <0.0001 |

Figure 5:
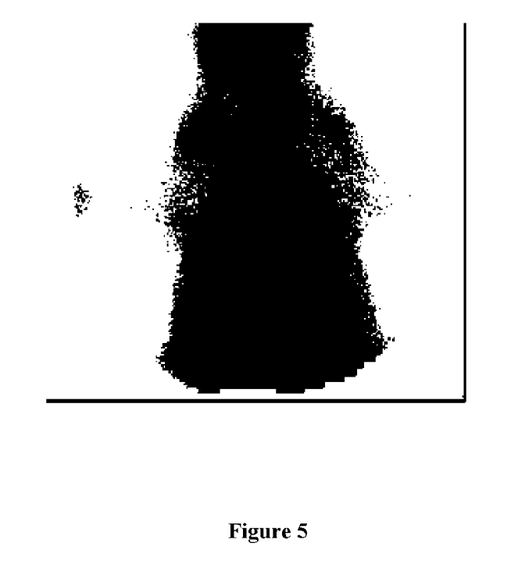
FIG. 5 shows ex vivo imaging of experimental left-sided endocarditis in rat

Of note, the pre-injection of 1 mg of non-labelled DOTA-G-dVFA-cmk in 3 animals did induce a decrease of the uptake intensity of 99mTc-DTPA-G-dVFKcmk (quantified by autoradiography: 6.43±1.85 vs 10.65±1.07 respectively, p=0.1 using Mann-Whitney U test). (FIG. 5)

Stroke in Rats:

In this model we compared the uptake of 99mTc-DTPA-G-dVFK-cmk with that of a the 99mTc chelate diethylenetriaminepentaacetic acid (DTPA), which is a non-specific tracer of capillary permeability.

A DOTA-G-dVFK-cmk stained by gadolinium (Gd) has been synthesized and injected in the model of stroke in rat (15 mg) for MRMolecular imaging. The MRI signal of the (Gd)-DOTA-G-dVFK-cmk was detectable and colocalized with the cerebral infarct in vivo and ex vivo.

The chelation was carried out by stoechiometric addition of the DOTA groups coupled to the VFK in the presence of GdCl$_3$, 6H$_2$O. After adjusting the pH to 6.5 in water, the solution was maintained at room temperature overnight followed by heating at 60° C. for 4 h. Free gadolinium was removed by dialysis against NaCl 0.1M then by dialysis against water through a 100 Da cut-off membrane. The product was freeze-dried. The reaction yield was about 88% in mass and nearly 100% in chelation. No free gadolinium was detected.

Figure 6:
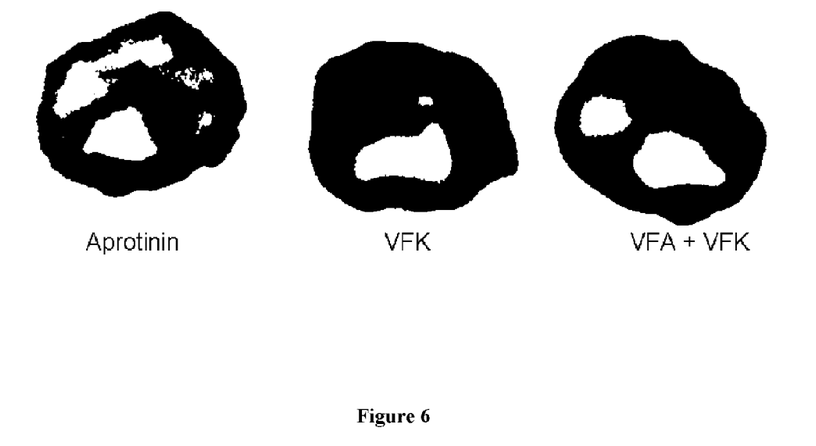
FIG. 6 shows intraluminal thrombus in human aneurysm of the abdominal aorta
Figure 7:
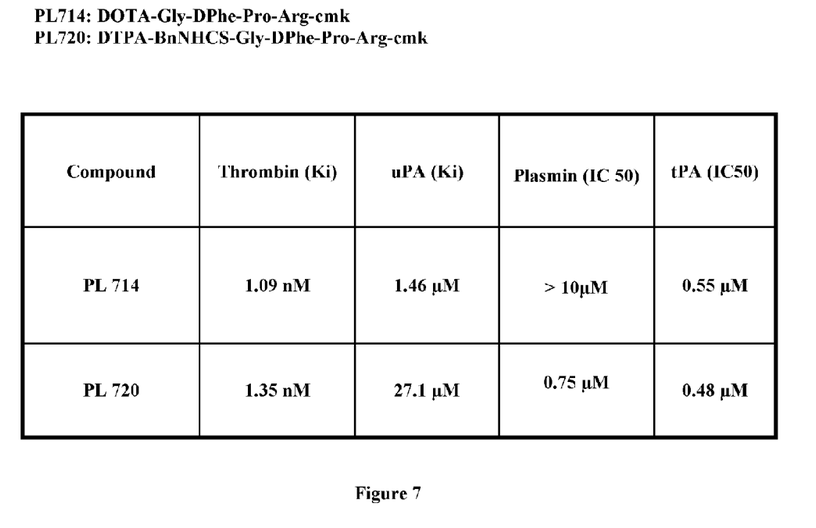
FIG. 7 shows the thrombin, uPA, and tPA inhibition of PL714, PL716, PL719, PL720: the dose-dependant inhibitory capacity of each molecule was evaluated in the presence of 20 ng/mL; 50 ng/mL, 1 μg/mL of thrombin, uPA and tPA respectively. Enzyme with or without inhibitors was pre-incubated at room temperature for 30 min, following by 60 min incubation. The fluorescent substrate (20 μM) was added just before reading (λ excitation 390 nM, λ emission 460 nM).
Figure 8:
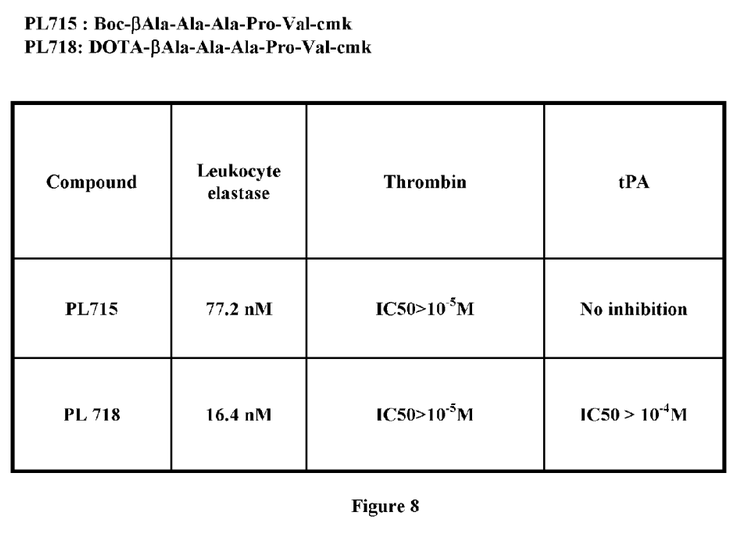
FIG. 8 shows the leukocyte elastase, thrombin and tPA inhibition of PL715, PL718: The dose-dependant inhibitory capacity of each molecule was evaluated in the presence of 30 ng/mL, 20 ng/mL and 1 μg/mL of leukocyte elastase, thrombin and tPA respectively. Enzyme with or without inhibitors was pre-incubated at room temperature for 30 min, following by 60 min incubation. The fluorescent substrate (20 μM) was added just before reading (λ excitation 390 nM, λ emission 460 nM).

Human Samples of Abdominal Aortic Aneurysms:

using 99mTc-Aprotinin as a control (Houard et al), human samples of AAA incubated in radiolabelled VFK showed a twofold increase of the activity. Autoradiography allowed evidencing a greater uptake both at the luminal and abluminal layers of the thrombus, but also within the intermediate layer. The latter may be related, at least in part, to the smaller size of 99mTc-DTPA-G-dVFKcmk (1 kDa) compared to 99mTc-Aprotinin (6 kDa) (FIG. 6).

In order to assess whether the higher tracer uptake at the luminal and abluminal layers of the thrombus was specific or merely due to the contact with the radio-labelled solution, prior to incubation with 99mTc-DTPA-G-dVFKcmk, a thrombus slice has been pre-incubated with a RPMI solution containing the non-specific analog DOTA-G-dVFA-cmk at a concentration of 0.05 mg/ml. The overall uptake of 99mTc-DTPA-G-dVFKcmk has been decreased by about 25%, but the ratio between the (ab)luminal layers and the intermediate layer remained unchanged.

In left ventricular endocarditis, 99mTc-DTPA-G-dVFKcmk gave localized positive image corresponding to the sceptic thrombus surrounding the catheter, and aortic valve and left ventricular myocardium positivity, which were confirmed by autoradiographies.

Similar images were obtained in right ventricular endocarditis, associated with detectable pulmonary emboli.

Histology:

Whatever the model, 99mTc-DTPA-G-dVFKcmk uptake was co-localized with the thrombus. Of note, in the endocarditis model, it was also co-localized with clusters of inflammatory cells within the myocardium.

Conclusions:

The new tracer radiolabelled DTPA-G-dVFK-cmk is able to report plasmin activity in pathologic tissues in various experimental models (AAA, left and right-sided endocarditis, stroke) as well as in human samples of mural thrombus in AAA. The uptake of the radiotracer is specific as evidenced by its significant decrease by the pre-injection of the non-labelled compound in the AAA model, by the lack of inhibition of its uptake by the pre-injection of the non-specific analog DOTA-G-dVFA-cmk in left-sided endocarditis and in human samples of AAA, and by the lower uptake intensity of the non-specific radiolabelled analog $^{111}$In-DOTA-G-dVFA-cmk.

REFERENCES

Throughout this application, various references describe the state of the art to which this invention pertains. The disclosures of these references are hereby incorporated by reference into the present disclosure.

The invention claimed is:

1. A serine protease-targeted molecular imaging agent comprising at least one irreversible peptide ligand of a serine protease bound to at least one detectable moiety via a spacer, wherein said serine protease is tissue plasminogen activator (tPA), and wherein said at least one irreversible peptide ligand has the general formula (II):

P—X1-Pro-Y1-Gly-Arg-cmk (II)

wherein:
P is a protective group,
X1 is Gly or Ala,
Y1 is Phe, Tyr, Ile or Leu, and
cmk is aminoacyl chloromethylketone.

2. A serine protease-targeted molecular imaging agent comprising at least one irreversible peptide ligand of a serine protease bound to at least one detectable moiety via a spacer, wherein said serine protease is plasmin, and wherein said at least one irreversible peptide ligand is D-Val-Phe-Lys-cmk, where -cmk is aminoacyl chloromethylketone.

3. A pharmaceutical composition comprising at least one serine protease-targeted molecular imaging agent according to claim 1 and at least one pharmaceutically acceptable carrier.

4. The serine protease-targeted molecular imaging agent of claim 1, wherein said protective group is Acetyl (Ac) or tButyloxycarbonyl (Boc).

5. A method of molecular imaging of tissue plasminogen activator (t-PA) or plasmin comprising
a) administering to a patient an effective amount of a serine protease-targeted molecular imaging agent comprising at least one irreversible peptide ligand of a serine protease bound to at least one detectable moiety via a spacer, wherein said serine protease is t-PA or plasmin, and whereby said serine-protease-targeted molecular imaging agent binds to t-PA or plasmin present in the patient;
wherein if said serine protease is t-PA then said at least one irreversible peptide ligand has the general formula (II):

P—X1-Pro-Y1-Gly-Arg-cmk (II)

wherein:
P is a protective group,
X1 is Gly or Ala,
Y1 is Phe, Tyr, Ile or Leu, and
cmk is aminoacyl chloromethylketone
or if said serine protease is plasmin, then said at least one irreversible peptide ligand is D-Val-Phe-Lys-cmk, where -cmk is aminoacyl chloromethylketone;
wherein said detectable moiety is detectable by a molecular imaging technique selected from the group consisting of Magnetic Resonance Imaging (MRI), planar scintigraphy (PS), Positron Emission Tomography (PET), Single Photon Emission Computed Tomography (SPECT), or any combination of these techniques and
b) detecting the serine protease-targeted molecular imaging agent bound to t-PA or plasmin present in the patient using said a molecular imaging technique.

6. A pharmaceutical composition comprising at least one serine protease-targeted molecular imaging agent according to claim 2 and at least one pharmaceutically acceptable carrier.

7. The serine protease-targeted molecular imaging agent of claim 1, wherein the at least one irreversible peptide ligand of a serine protease is covalently bound through a Gly residue with a metal-chelating moiety.

8. The serine protease-targeted molecular imaging agent of claim 2, wherein the at least one irreversible peptide ligand of a serine protease is covalently bound through a Gly residue with a metal-chelating moiety.

9. The serine protease-targeted molecular imaging agent of claim 7, wherein the metal-chelating moiety is 1,4,7,10-tetraazacyclododecane-N,N',N'',N'''-tetraacetic acid (DOTA), diethylene triaminepentaacetic acid (DTPA), 1,4,7-triaza-cyclononane N,N',N''-triacetic acid (NOTA) or 6-hydrazinopyridine-3-carboxylic acid (HYNIC).

10. The serine protease-targeted molecular imaging agent of claim 8, wherein the metal-chelating moiety is 1,4,7,10-tetraazacyclododecane-N,N',N'',N'''-tetraacetic acid (DOTA), diethylene triaminepentaacetic acid (DTPA), 1,4,7-triaza-cyclononane N,N',N''-triacetic acid (NOTA) or 6-hydrazinopyridine-3-carboxylic acid (HYNIC).

11. The serine protease-targeted molecular imaging agent of claim 7, wherein the metal-chelating moiety is complexed with a radionuclide metal or a paramagnetic metal ion.

12. The serine protease-targeted molecular imaging agent of claim 8, wherein the metal-chelating moiety is complexed with a radionuclide metal or a paramagnetic metal ion.

13. The serine protease-targeted molecular imaging agent of claim 11, wherein the radionuclide metal is gallium-68 (68Ga), technetium-99m (99mTc), gallium-67 (67Ga), yttrium-91 (91Y), indium-111 (111 In), rhenium-186 (186Re), or thallium-201 (201 Tl).

14. The serine protease-targeted molecular imaging agent of claim 11, wherein the paramagnetic metal ion is gadolinium III (Gd3+).

15. The serine protease-targeted molecular imaging agent of claim 12, wherein the radionuclide metal is technetium-99m (99mTc), gallium-67 (67Ga), yttrium-91 (91Y), indium-111 (111 In), rhenium-186 (186Re), or thallium-201 (201Tl).

16. The serine protease-targeted molecular imaging agent of claim 12, wherein the paramagnetic metal ion is gadolinium III (Gd3+).

17. The serine protease-targeted molecular imaging agent of claim 1, wherein the at least one irreversible peptide ligand of a serine protease is covalently bound through a benzylthiourea with a metal-chelating moiety.

18. The serine protease-targeted molecular imaging agent of claim 2, wherein the at least one irreversible peptide ligand of a serine protease is covalently bound through a benzylthiourea with a metal-chelating moiety.

19. The serine protease-targeted molecular imaging agent of claim 17, wherein the metal-chelating moiety is DOTA, DTPA or NOTA.

20. The serine protease-targeted molecular imaging agent of claim 18, wherein the metal-chelating moiety is DOTA, DTPA or NOTA.

* * * * *